(12) United States Patent
Greener

(10) Patent No.: US 8,791,316 B2
(45) Date of Patent: Jul. 29, 2014

(54) WOUND PACKING

(75) Inventor: Bryan Greener, York (GB)

(73) Assignee: Smith & Nephew PLC, London (GB)

( * ) Notice: Subject to any disclaimer, the term of this patent is extended or adjusted under 35 U.S.C. 154(b) by 108 days.

(21) Appl. No.: 13/201,427

(22) PCT Filed: Feb. 10, 2010

(86) PCT No.: PCT/GB2010/000228
§ 371 (c)(1),
(2), (4) Date: Sep. 14, 2011

(87) PCT Pub. No.: WO2010/092334
PCT Pub. Date: Aug. 19, 2010

(65) Prior Publication Data
US 2011/0319804 A1   Dec. 29, 2011

(30) Foreign Application Priority Data
Feb. 13, 2009 (GB) .................................. 0902368.0

(51) Int. Cl.
*A61F 13/00* (2006.01)
*A61L 15/42* (2006.01)
*A61F 15/00* (2006.01)
*A61F 13/02* (2006.01)
*A61M 1/00* (2006.01)

(52) U.S. Cl.
CPC ......... *A61L 15/425* (2013.01); *A61F 13/00987* (2013.01); *A61F 15/001* (2013.01); *A61F 13/0276* (2013.01); *A61M 1/0088* (2013.01)
USPC .............. 602/46; 604/304; 604/319; 604/369; 604/378

(58) Field of Classification Search
CPC ................ A61F 13/00; A61F 13/0276; A61F 13/15203; A61F 13/0203; A61M 1/0088; A61M 1/0013; A61M 1/0001; A61L 15/425; A61L 15/001; A61L 2300/404
USPC .............. 602/41–59; 604/289–290, 304–306, 604/319, 369, 378
See application file for complete search history.

(56) References Cited

U.S. PATENT DOCUMENTS

| 1,066,934 A | 7/1913 | Manney |
| 1,975,504 A | 10/1934 | Formhals |

(Continued)

FOREIGN PATENT DOCUMENTS

| DE | 3539533 A1 | 5/1987 |
| EP | 0122085 B1 | 6/1987 |

(Continued)

OTHER PUBLICATIONS

International Search Report for International Application No. PCT/GB2010/000228, mailed May 12, 2010 in 6 pages.

(Continued)

*Primary Examiner* — Kim M Lewis
(74) *Attorney, Agent, or Firm* — Knobbe, Martens, Olson & Bear LLP

(57) ABSTRACT

The present invention relates to a wound packing material that comprises a porous material and is suitable for use in negative pressure wound therapy. The wound packing material comprises frangible regions defining a plurality of portions, the frangible regions allowing the portions to be selectively removed. The invention further relates to methods of manufacturing the wound packing material, and to methods of its use.

37 Claims, 4 Drawing Sheets

(56) References Cited

U.S. PATENT DOCUMENTS

| | | | |
|---|---|---|---|
| 2,877,765 A | 3/1959 | Bunyan |
| 4,252,119 A | 2/1981 | Coates |
| 4,294,240 A | 10/1981 | Thill |
| 4,341,207 A | 7/1982 | Steer et al. |
| 4,360,015 A | 11/1982 | Mayer |
| 4,360,021 A | 11/1982 | Stima |
| 4,418,691 A | 12/1983 | Yannas et al. |
| 4,499,896 A | 2/1985 | Heinecke |
| 4,541,426 A | 9/1985 | Webster |
| 4,561,435 A | 12/1985 | McKnight et al. |
| 4,664,662 A | 5/1987 | Webster |
| 4,699,134 A | 10/1987 | Samuelsen |
| 4,759,354 A | 7/1988 | Quarfoot |
| 4,798,603 A | 1/1989 | Meyer et al. |
| 4,867,150 A | 9/1989 | Gilbert |
| 4,875,473 A | 10/1989 | Alvarez |
| 4,882,213 A | 11/1989 | Gaddis et al. |
| 4,929,477 A | 5/1990 | Will |
| 4,969,880 A | 11/1990 | Zamierowski |
| 4,997,425 A | 3/1991 | Shioya et al. |
| 5,080,661 A | 1/1992 | Lavender et al. |
| 5,149,331 A | 9/1992 | Ferdman et al. |
| 5,167,613 A | 12/1992 | Karami et al. |
| 5,218,973 A | 6/1993 | Weaver et al. |
| 5,261,893 A | 11/1993 | Zamierowski |
| 5,264,218 A | 11/1993 | Rogozinski |
| 5,267,952 A | 12/1993 | Gardner |
| 5,322,695 A | 6/1994 | Shah et al. |
| 5,336,209 A | 8/1994 | Porzilli |
| 5,397,316 A | 3/1995 | LaVon et al. |
| 5,415,715 A | 5/1995 | Delage et al. |
| 5,445,604 A | 8/1995 | Lang |
| 5,486,158 A | 1/1996 | Samuelson |
| 5,489,304 A | 2/1996 | Orgill et al. |
| 5,496,605 A | 3/1996 | Augst et al. |
| 5,527,293 A | 6/1996 | Zamierowski |
| 5,549,584 A | 8/1996 | Gross |
| 5,593,395 A | 1/1997 | Martz |
| 5,599,289 A | 2/1997 | Castellana |
| 5,616,387 A | 4/1997 | Augst et al. |
| 5,626,954 A * | 5/1997 | Andersen et al. .......... 428/294.7 |
| 5,633,007 A | 5/1997 | Webb et al. |
| 5,636,643 A | 6/1997 | Argenta et al. |
| 5,645,081 A | 7/1997 | Argenta et al. |
| 5,681,579 A | 10/1997 | Freeman |
| 5,713,881 A | 2/1998 | Rezai et al. |
| 5,714,225 A | 2/1998 | Hansen et al. |
| 5,716,411 A | 2/1998 | Orgill et al. |
| 5,720,714 A | 2/1998 | Penrose |
| 5,733,305 A | 3/1998 | Fleischmann |
| 5,759,570 A | 6/1998 | Arnold |
| 5,792,090 A | 8/1998 | Ladin |
| 5,810,755 A | 9/1998 | LeVeen et al. |
| D403,774 S | 1/1999 | Laughlin et al. |
| 5,868,724 A | 2/1999 | Diercket et al. |
| 5,885,237 A | 3/1999 | Kadash et al. |
| D408,920 S | 4/1999 | Dunshee et al. |
| 5,899,893 A | 5/1999 | Dyer et al. |
| 5,958,420 A | 9/1999 | Jenson |
| D415,836 S | 10/1999 | Dunshee et al. |
| 5,981,822 A | 11/1999 | Addison |
| 5,985,990 A | 11/1999 | Kantner et al. |
| 6,071,267 A | 6/2000 | Zamierowski |
| 6,087,549 A | 7/2000 | Flick |
| 6,117,111 A | 9/2000 | Fleischmann |
| 6,142,982 A | 11/2000 | Hunt et al. |
| 6,167,613 B1 | 1/2001 | Karmi |
| 6,203,563 B1 | 3/2001 | Fernandez |
| 6,203,654 B1 | 3/2001 | McFall et al. |
| 6,293,281 B1 | 9/2001 | Shultz et al. |
| 6,333,093 B1 | 12/2001 | Burrell et al. |
| 6,345,623 B1 | 2/2002 | Heaton et al. |
| 6,350,339 B1 | 2/2002 | Sessions |
| 6,398,767 B1 | 6/2002 | Fleischmann |
| 6,447,799 B1 | 9/2002 | Ullman |
| 6,458,109 B1 | 10/2002 | Henley |
| 6,553,998 B2 | 4/2003 | Heaton et al. |
| 6,680,113 B1 | 1/2004 | Lucast et al. |
| 6,685,681 B2 | 2/2004 | Lockwood et al. |
| 6,713,659 B2 | 3/2004 | Bodenschatz et al. |
| 6,752,794 B2 | 6/2004 | Lockwood et al. |
| 6,767,334 B1 * | 7/2004 | Randolph ....................... 604/35 |
| 6,794,554 B2 | 9/2004 | Sessions et al. |
| 6,797,855 B2 | 9/2004 | Worthley |
| 6,814,079 B2 | 11/2004 | Heaton et al. |
| 6,838,589 B2 | 1/2005 | Liedtke et al. |
| 6,855,135 B2 | 2/2005 | Lockwood et al. |
| D506,547 S | 6/2005 | Cruz et al. |
| 6,942,628 B1 | 9/2005 | Watson |
| 6,951,553 B2 | 10/2005 | Bubb et al. |
| 6,974,428 B2 | 12/2005 | Knutson et al. |
| 7,004,915 B2 | 2/2006 | Boynton et al. |
| 7,005,556 B1 | 2/2006 | Becker et al. |
| 7,030,288 B2 | 4/2006 | Liedtke et al. |
| 7,041,868 B2 | 5/2006 | Greene et al. |
| 7,108,681 B2 | 9/2006 | Gartstein et al. |
| 7,108,683 B2 | 9/2006 | Zamierowski |
| 7,122,712 B2 | 10/2006 | Lutri et al. |
| 7,137,968 B1 | 11/2006 | Burrell et al. |
| D537,948 S | 3/2007 | Smith |
| D544,607 S | 6/2007 | Henry et al. |
| 7,291,762 B2 | 11/2007 | Flick |
| 7,335,809 B2 | 2/2008 | Riesinger |
| 7,338,482 B2 | 3/2008 | Lockwood et al. |
| 7,381,859 B2 | 6/2008 | Hunt et al. |
| 7,438,705 B2 | 10/2008 | Karpowicz et al. |
| 7,494,482 B2 | 2/2009 | Orgill et al. |
| 7,518,031 B2 | 4/2009 | Liedtke et al. |
| 7,645,269 B2 | 1/2010 | Zamierowski |
| 7,676,400 B1 | 3/2010 | Dillon |
| 7,676,784 B2 | 3/2010 | Allen et al. |
| 7,722,582 B2 | 5/2010 | Lina et al. |
| D620,122 S | 7/2010 | Cotton |
| D620,123 S | 7/2010 | Igwebuike |
| 7,754,937 B2 | 7/2010 | Boehringer et al. |
| 7,790,946 B2 | 9/2010 | Mulligan |
| 7,794,438 B2 | 9/2010 | Henley et al. |
| 7,846,141 B2 | 12/2010 | Weston |
| 7,896,856 B2 | 3/2011 | Petrosenko et al. |
| 7,909,805 B2 | 3/2011 | Weston |
| D639,441 S | 6/2011 | Sferle |
| 7,982,087 B2 | 7/2011 | Greener et al. |
| D644,330 S | 8/2011 | Pfeiffer et al. |
| 8,062,272 B2 | 11/2011 | Weston |
| 8,062,331 B2 | 11/2011 | Zamierowski |
| 8,070,773 B2 | 12/2011 | Zamierowski |
| RE43,195 E | 2/2012 | Cotton |
| 8,338,402 B2 | 12/2012 | Fry et al. |
| 2001/0027285 A1 | 10/2001 | Heinecke et al. |
| 2001/0034499 A1 | 10/2001 | Sessions et al. |
| 2002/0065494 A1 | 5/2002 | Lockwood et al. |
| 2002/0082567 A1 | 6/2002 | Lockwood et al. |
| 2002/0161346 A1 | 10/2002 | Lockwood et al. |
| 2002/0193721 A1 | 12/2002 | Vandruff |
| 2003/0050590 A1 | 3/2003 | Kirsch |
| 2003/0050594 A1 | 3/2003 | Zamierowski |
| 2003/0108587 A1 | 6/2003 | Orgill et al. |
| 2004/0006319 A1 | 1/2004 | Lina et al. |
| 2004/0019337 A1 | 1/2004 | Moberg-Alehammar et al. |
| 2004/0064111 A1 | 4/2004 | Lockwood et al. |
| 2004/0162512 A1 | 8/2004 | Liedtke et al. |
| 2005/0090860 A1 * | 4/2005 | Paprocki ....................... 606/213 |
| 2005/0113733 A1 | 5/2005 | Liedtke et al. |
| 2005/0131327 A1 | 6/2005 | Lockwood et al. |
| 2005/0143697 A1 | 6/2005 | Riesinger |
| 2005/0181163 A1 | 8/2005 | Kose |
| 2005/0215932 A1 | 9/2005 | Sigurjonsson et al. |
| 2006/0041247 A1 | 2/2006 | Petrosenko et al. |
| 2006/0142687 A1 | 6/2006 | Liedtke et al. |
| 2006/0161123 A1 | 7/2006 | Kudo et al. |
| 2006/0178608 A1 | 8/2006 | Stapf |
| 2006/0241689 A1 | 10/2006 | Leiboff et al. |
| 2007/0010775 A1 | 1/2007 | Lutri |
| 2007/0032763 A1 | 2/2007 | Vogel |

(56) References Cited

U.S. PATENT DOCUMENTS

| | | |
|---|---|---|
| 2007/0142761 A1 | 6/2007 | Aali |
| 2007/0185426 A1 | 8/2007 | Ambrosio et al. |
| 2007/0185463 A1 | 8/2007 | Mulligan |
| 2008/0095979 A1 | 4/2008 | Hatanaka et al. |
| 2008/0167593 A1 | 7/2008 | Fleischmann |
| 2008/0213344 A1 | 9/2008 | McCarthy et al. |
| 2008/0243044 A1 | 10/2008 | Hunt et al. |
| 2008/0300555 A1 | 12/2008 | Olson et al. |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0105671 A1 | 4/2009 | Daggar et al. |
| 2009/0130186 A1 | 5/2009 | McCarthy et al. |
| 2009/0177136 A1 | 7/2009 | Liedtke et al. |
| 2009/0227969 A1 | 9/2009 | Jaeb et al. |
| 2009/0240185 A1 | 9/2009 | Jaeb et al. |
| 2010/0010462 A1 | 1/2010 | Kurata |
| 2010/0069829 A1 | 3/2010 | Hutchinson et al. |
| 2010/0069858 A1 | 3/2010 | Olson |
| 2010/0069885 A1 | 3/2010 | Stevenson et al. |
| 2010/0100022 A1 | 4/2010 | Greener et al. |
| 2010/0106115 A1 | 4/2010 | Hardman et al. |
| 2010/0106117 A1 | 4/2010 | Lockwood et al. |
| 2010/0179463 A1 | 7/2010 | Greener et al. |
| 2010/0196106 A1 | 8/2010 | Allen |
| 2010/0249733 A9 | 9/2010 | Blott |
| 2010/0318046 A1 | 12/2010 | Boehringer et al. |
| 2011/0178451 A1 | 7/2011 | Robinson et al. |
| 2011/0213287 A1 | 9/2011 | Lattimore |
| 2012/0041402 A1 | 2/2012 | Greener |
| 2012/0130326 A1 | 5/2012 | Cavanaugh, II et al. |

FOREIGN PATENT DOCUMENTS

| | | |
|---|---|---|
| EP | 0418607 A1 | 3/1991 |
| EP | 0485657 A1 | 5/1992 |
| EP | 0617938 A1 | 10/1994 |
| EP | 0638301 A1 | 2/1995 |
| EP | 0465601 B1 | 1/1997 |
| EP | 0762860 B1 | 12/1997 |
| EP | 0651983 B1 | 9/1998 |
| EP | 0777504 B1 | 10/1998 |
| EP | 0688189 B1 | 9/2000 |
| EP | 0670705 B1 | 5/2001 |
| EP | 0865304 B1 | 7/2001 |
| EP | 0875222 B1 | 7/2002 |
| EP | 0853950 B1 | 10/2002 |
| EP | 1088569 B1 | 8/2003 |
| EP | 1219311 B1 | 7/2004 |
| EP | 1018967 B1 | 8/2004 |
| EP | 1614789 A1 | 1/2006 |
| EP | 1440667 B1 | 3/2006 |
| EP | 1284777 B1 | 4/2006 |
| EP | 0620720 B2 | 11/2006 |
| EP | 1772160 B1 | 6/2009 |
| EP | 1513478 B1 | 12/2009 |
| EP | 2214728 B1 | 6/2012 |
| GB | 821959 A | 10/1959 |
| GB | 1063066 A | 3/1967 |
| GB | 1224009 A | 3/1971 |
| GB | 2085305 A | 1/1985 |
| GB | 2195255 A | 4/1988 |
| GB | 2329127 B | 3/1999 |
| GB | 2305610 B | 7/1999 |
| GB | 2357286 B | 11/2003 |
| GB | 2 389 794 A | 12/2003 |
| GB | 2389794 A | 12/2003 |
| GB | 2365350 B | 8/2004 |
| GB | 2423019 A | 8/2006 |
| JP | H02-139624 | 11/1990 |
| JP | H02-139625 | 11/1990 |
| JP | H06-339495 | 12/1994 |
| JP | H11-056900 | 3/1999 |
| JP | 2004-000465 | 1/2004 |
| WO | WO 90/10424 A1 | 9/1990 |
| WO | WO 92/10983 A1 | 7/1992 |
| WO | WO 92/13713 A1 | 8/1992 |
| WO | WO 93/00056 A1 | 1/1993 |
| WO | WO 94/20041 A1 | 9/1994 |
| WO | WO 95/14451 A1 | 6/1995 |
| WO | WO 96/01731 A1 | 1/1996 |
| WO | WO 96/24316 A1 | 8/1996 |
| WO | WO 97/11658 A1 | 4/1997 |
| WO | WO 97/43991 A1 | 11/1997 |
| WO | WO 98/38955 A1 | 9/1998 |
| WO | WO 00/07653 A1 | 2/2000 |
| WO | WO 00/61206 A1 | 10/2000 |
| WO | WO 01/49233 A1 | 7/2001 |
| WO | WO 01/85248 A1 | 11/2001 |
| WO | WO 02/05737 A1 | 1/2002 |
| WO | WO 02/26180 A1 | 4/2002 |
| WO | WO 02/39940 A2 | 5/2002 |
| WO | WO 02/41878 A2 | 5/2002 |
| WO | WO 02/45761 A1 | 6/2002 |
| WO | WO 02/091965 A1 | 11/2002 |
| WO | WO 02/092783 A2 | 11/2002 |
| WO | WO 03/051409 A1 | 6/2003 |
| WO | WO 03/072748 A2 | 9/2003 |
| WO | WO 03/086232 A2 | 10/2003 |
| WO | WO 2004/018020 A1 | 3/2004 |
| WO | WO 2005/009488 A2 | 2/2005 |
| WO | WO 2006/099137 A1 | 9/2006 |
| WO | WO 2006/130594 A2 | 12/2006 |
| WO | WO 2007/075379 A2 | 7/2007 |
| WO | WO 2008/039839 A2 | 4/2008 |
| WO | WO 2008/040681 A1 | 4/2008 |
| WO | WO 2008/064503 A1 | 6/2008 |
| WO | WO 2008/104609 A1 | 9/2008 |
| WO | WO 2008/141228 A1 | 11/2008 |
| WO | WO 2009/011856 A1 | 1/2009 |
| WO | WO 2009/021523 A1 | 2/2009 |
| WO | WO 2009/070905 A1 | 6/2009 |
| WO | WO 2009/158131 A1 | 12/2009 |
| WO | WO 2010/010398 A1 | 1/2010 |
| WO | WO 2010/016791 A1 | 2/2010 |
| WO | WO 2010/033271 A1 | 3/2010 |
| WO | WO 2010/033574 A1 | 3/2010 |
| WO | WO 2010/033613 A1 | 3/2010 |
| WO | WO 2010/051068 A1 | 5/2010 |
| WO | WO 2010/051073 A1 | 5/2010 |
| WO | WO 2010/072309 A1 | 7/2010 |
| WO | WO 2011/106722 A1 | 9/2011 |
| WO | WO 2012/138514 A1 | 10/2012 |

OTHER PUBLICATIONS

Design U.S. Appl. No. 29/363,038, including its ongoing prosecution history, including without limitation Office Actions, Amendments, Remarks, and any other potentially relevant documents, filed Jun. 3, 2010, Lattimore et al.

U.S. Appl. No. 14/035,487, filed Sep. 24, 2013, Greener et al.

"Hydrocolloids," J. of Wound Care, vol. 1, No. 2, (Jul.-Aug. 1992), pp. 27-30.

Alexander, J. Wesley, et al., Clinical Evaluation of Epigard, A New Synthetic Substitute for Homograft and Heterograft Skin, The Journal of Trauma, vol. 13, No. 4, 1973, pp. 374-383.

Applications for Modification to HCPCS Level II Code Set in the 2005-2006 Coding Cycle. Www.cms.hhs.gov/medicare/hcpcs/.

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96.

Barker et al., "Vacuum Pack Technique of Temporary Abdominal Closure"; J. of Traumatic Injury, Infection, and Critical Care, vol. 48, No. 2 (2000).

Blumberg, et al., The Effect of Specific Compression on Soft-Tissue Response to Formalinized PVA (Ivalon) Sponge: A Critical Evaluation, Annals Surg., Mar. 1960, 151(3), 409-418.

Boland E.D. et al. Utilizing acid pre-treatment and electrospinning to improve biocompatibility poly(glycolic acid) for tissue engineering. J. Biomed. Mater. Res. Part B: Appl Biomater 71B 144-152, 2004.

(56) References Cited

OTHER PUBLICATIONS

Boland et al., "Tailoring Tissue Engineering Scaffolds Using Electrostatic Processing Techniques: A Study of Poly(Glycolic Acid) Electrospinning" Journal of Macromolecular Science A. Pure and Applied Chemistry, A38(12), 1231-1243 (2001).
Brock, W.B., et al.: "Temporary closure of open abdominal wounds: the vacuum pack", Am. Surg. Jan. 1995; 61(1)30-5—abstract.
Fleischmann et al., "Vacuum sealing for treatment of soft tissue damage in open fractures," Der Unfallchirurg 1993;96(9):488-92.
Garner et al., "Vacuum-assisted wound closure provides early fascial reapproximation in trauma patients with open abdomens," Am. J. of Surgery 1282 (2001) 630-638.
Harris, "A new technique of skin grafting using Stei-Greffe and a self-adhering foam pad," Brit. J. of Plastic Surg., vol. 34, No. 2, (Apr. 1981), pp. 181-185.
Jeter, K. "Managing Draining Wounds and Fistulae: New and Established Methods" Chronic Wound Care pp. 240-246, 1990.
KCI Licensing, "V.A.C. Abdominal Dressing System Advanced Management of the Open Abdomen," 2004.
KCI V.A.C. Simplace Dressing Brochure 2008, in 2 pages.
Ma, Peter X. Scaffolds for tissue fabrication. Materials Today, Review, May 2004.
Middleton, J., A. Tipton (Mar. 1998). "Synthetic biodegradable polymers as medical devices" (HTML). Medical Plastics and Biomaterials Magazine.
Navsaria, et al.: "Temporary closure of open abdominal wounds by the modified sandwich-vacuum pack technique", British Journal of Surgery 2003; 90: 718-722.
Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on the Open Abdomen in General Surgery—How Do You Close the Abdomen When You Can't—Boston Marriott Copley Place Hotel, Boston, MA Apr. 26, 2004.
Orgill, D.P., et al., Guidelines for Treatment of Complex Chest Wounds with Negative Pressure Wound Therapy, *Wounds, A Compendium of Clinical Research and Practice*, Suppl. B, Dec. 2004, 1-23.
Schein et al., "The 'Sandwich Technique' in the Management of the Open Abdomen," British Journal of Surgery, 1986, vol. 73, May, pp. 369-370.
Smith, et al.; Vacuum Pack Technique of Temporary Abdominal Closure: A Four-Year Experience; The American Surgeon; Dec. 1997; p. 1102-1108; vol. 63, No. 12.
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).

* cited by examiner

The blade length (end to end of each cross) is 18 mm

WOUND PACKING

CROSS-REFERENCE TO RELATED APPLICATIONS

This application is a U.S. National Phase of PCT International Application No. PCT/GB2010/000228, filed on Feb. 10, 2010, designating the United States and published on Aug. 19, 2010 as WO 2010/092334, which claims priority to Great Britain Patent Application No. 0902368.0, filed on Feb. 13, 2009. The disclosure of both prior applications are incorporated by reference herein in their entireties and should be considered a part of this application.

BACKGROUND OF THE DISCLOSURE

1. Field of the Invention

The present invention relates to a porous wound packing material and methods of its manufacture and use. In particular it relates to a wound packing material which is adapted to allow it to be easily shaped and configured to the shape of a wound. Such wound packing materials are particularly suitable for negative pressure wound therapy (NPWT).

2. Background

NPWT is a relatively new treatment for open wounds. Typically in NPWT the wound cavity or surface is filled or covered with a material that allows the transmission of a partial vacuum (i.e. does not completely collapse) to the wound bed when a negative pressure is applied to the wound area, and also allows fluids to pass from the wound bed towards the source of negative pressure. There are two primary approaches to NPWT, i.e. gauze or foam types. The gauze type (also referred to as the Chariker-Jeter technique) involves the use of a drain wrapped in gauze topped by a sealed dressing. The foam type involves the use of foam placed over or in the wound. The present invention is directed primarily towards the foam type of NPWT.

In foam based NPWT the wound cavity is filled or covered with a porous foam packing material and covered over and sealed with flexible sheet (a drape) that is fairly impermeable to fluids. A tube is inserted under or through the drape into the wound site and its distal end is connected to a vacuum source (commonly a pump). The wound cavity, enclosed by the drape and tissue, contracts under the force of atmospheric pressure and compresses the packing material visibly. Gross tissue movement ceases after a few tens of seconds and fluid flow from the wound (withdrawn from the tissue) ensues. The fluid is transmitted through the packing material and up the vacuum tube to a collection receptacle positioned between the distal end of the tube and the vacuum source. The wound packing material mechanically supports the tissue to which it is applied, and also allows the free flow of fluids away from the site when a vacuum is applied, even when compressed. A good material for this application is hydrophobic, reticulated polyurethane foam of very high free internal volume.

The packing material for use in NPWT must be shaped to fit the wound to be packed. This is typically achieved by the medical practitioner (typically physician or nurse) cutting a preformed block of foam (usually a cuboid) to approximately fit the Wound using a scalpel, knife or scissors. This operation can be complex, time consuming and messy for the medical practitioner, and indeed can be dangerous with the possibility of particulate foam material contaminating the wound site or of an accident during the cutting process. Accordingly, the process of shaping the wound dressing is currently an unaddressed problem in the field of NPWT which is a barrier to its effective and widespread use.

SUMMARY OF SOME EXEMPLIFYING EMBODIMENTS

According to the present invention there is provided a wound packing material comprising a body of a porous material, the body comprising frangible regions defining a plurality of portions, the frangible regions allowing the portions to be selectively removed from the body.

The term frangible is intended to mean that the material has been weakened in some manner which allows the portion to be removed relatively easily (e.g. manually) from the body without substantially damaging the remainder of the body, but where the overall structure of the body is sufficiently strong that the body remains intact during normal use, i.e. in the absence of manipulation to remove a portion. It is highly preferred that the portions can be removed manually, without the use of additional tools such as scissors, knives, scalpels etc. This allows a medical practitioner to remove portions to achieve a desired shape of the body quickly and simply without the need to use additional tools.

Preferably the frangible regions are defined by partial pre-cuts formed in the body.

Use of the term partial pre-cuts is intended to mean a region of the body where the material of the body has been removed or severed to at least partially separate a portion of the body from the rest of the body, but where sufficient material of the body, has been left such that the body retains its general structural integrity, i.e. sufficient integrity for general storage, handling and use as a wound packing material. However, the remaining material is sufficiently weak (i.e. frangible) that it is relatively easily severable with manually applied force, e.g. by a medical practitioner tearing the portion from the body.

It should be noted that the term partial pre-cuts is intended to cover both situation where material is removed by cutting or otherwise removing or severing regions of a preformed body of porous material, and also where the pre-cuts are formed during initial production of the body, e.g. formed during a moulding process.

Preferably the wound packing material is a wound packing foam suitable for use in negative pressure wound therapy (NPWT). Particularly suitable foams for NPWT include polyurethane foam, typically reticulated polyurethane foam of very high free internal volume, e.g. 80% or higher, preferably 90% or higher free internal volume. Typical foams used in NPWT have porosities in the range 30-60 ppi (pores per inch) and pore diameters in the range 300-800 µm. However, other suitable foams are known in the art and may be equally suitable. In general suitable foams have an open porous structure, to allow transmission of the negative pressure to the wound bed, and sufficient mechanical strength to prevent the negative pressure (typically approximately 80-125 mm Hg below ambient atmospheric pressure) from substantially collapsing the structure of the foam.

It is highly preferred that the wound packing material is sterile. This can be achieved using conventional sterilisation techniques which are known for sterilising surgical foams and dressings.

It will be clear to the person skilled in the art that size and shape of the selectively removable portions will be determined by the number of frangible regions provided per unit volume of the body, and the number of different orientations and configurations that the frangible regions are provided in.

As mentioned above, the frangible regions are preferably defined by partial pre-cuts within the body—the following description will focus on embodiments whereby the frangible regions are formed in this way, but it will be understood that frangible regions could be formed in other manners (e.g. selectively weakening the foam structure at selected regions using chemically agents or heat) and that such variants are within the scope of the present invention.

It is preferred that the partial pre-cuts are generally planar. In particular, flat planar partial pre-cuts are preferred as they provide for regularly shaped portions. However, it is perfectly possible that the planes could be curved where a curved profile on an exposed region of the body following removal of the portions is preferred.

Suitably the body comprises a first set of substantially parallel planar partial pre-cuts in first orientation. The set may comprise a plurality of planar pre-cuts, each planar pre-cut comprising a series of individual pre-cuts, each individual pre-cut being spaced from the adjacent pre-cut by a gap. The individual pre-cuts are aligned with the plane defined by the planar parallel partial pre-cut. Preferably the parallel planar partial pre-cuts of the set are regularly spaced. Where one set of parallel planar partial pre-cuts is provided in a single orientation it will be apparent that the removable portions defined by the set of planar partial pre-cuts will be slices of the body; each slice is removable from the next slice as a result of the planar parallel partial pre-cut between them.

It is preferred that the spacing between each of the parallel planar pre-cuts in the set is 30 mm or less, preferably 25 mm or less, especially 20 mm or less, and optionally 15 mm or less. The size of the portions are defined by the spacing between the parallel planar pre-cuts in the set—in this case the slices would have a thickness corresponding to the spacing between each plane.

The partial pre-cuts sever a substantial amount of the material in the plane being cut, leaving one or more relatively narrow pieces of material attaching the portion to the body (i.e. a gap), the relatively narrow piece of material thus forming the frangible region. It is desirable that the partial pre-cuts define a repeating pattern of severed regions with intervening frangible regions, i.e. perforation. It is preferred that the severed regions have a width of from 10 mm to 30 mm, preferably from 15 mm to 25 mm, and optionally from 16 to 22 mm, especially around 18 mm, and that the remaining frangible regions have a width of from 1 mm to 5 mm, preferably 1 to 3 mm, especially around 2 mm.

In another way of considering the spacing and size of the individual partial pre-cuts, typically the ratio of length of severed material to remaining material will be around 3 to 1 or higher (e.g. 15 mm severed and 5 mm remaining, or a ratio equivalent thereof), preferably 6 to 1 or higher (e.g. 18 mm severed and 3 mm remaining, or a ratio equivalent thereof), especially 9 to 1 or higher (e.g. 18 mm severed and 2 mm remaining, or a ratio equivalent thereof).

In a particularly preferred embodiment the pre-cut severs from 15 to 19 mm and leaves a frangible region of from 1 to 5 mm, preferably 17 to 19 mm and leaves a frangible region of from 1 to 3 mm, and especially approximately 18 mm leaving a frangible region of approximately 2 mm width.

Conveniently such a cut can be made using a die cutting apparatus comprising an array of a set of parallel planar blades, the set comprising a plurality of series of blades arranged in a plane, each blade having a width corresponding to the width of the region to be severed, and a spacing between the adjacent blades within a series corresponding to the width of the frangible region. The spacing between each planar series of blades defines the thickness of the frangible portion.

Thus in a preferred embodiment of the invention, the wound packing material comprises partial pre-cuts formed by die-cutting. Alternative methods of forming the partial pre-cuts such as laser cutting or high pressure fluid cutting might be used as alternatives to die-cutting.

It is preferred that the body comprises a second set of parallel planar partial pre-cuts in a second orientation. Again, it is preferred that the partial pre-cuts are regularly spaced, and the dimensions set out above in relation to the first set of partial parallel planar pre-cuts are equally applicable to the second set.

The second set of partial pre-cuts may also be made by die cutting.

The second set may suitably provided at a second orientation which is substantially perpendicular to the first orientation, i.e. where the first second sets of pre-cuts intersect, it will be substantially at a right angle. The pre-cuts of the first and second sets could thus be said to lie on nominal X and Y planes respectively.

It will be apparent that where two sets of pre-cuts are provided, the selectively removable portions will typically be smaller than where one set of partial pre-cuts is provided, i.e. the second set will sub-divide the portions formed by the first set. Thus it could be said that the body has a higher volumetric resolution in that it is split into finer units.

Generally the shape of portion provided when a first and second set of partial pre-cuts is used will be substantially a cuboid, the width and breadth of which is defined by the spacing of the planes in each of the partial pre-cuts, the length being defined by the relative dimension of the body in a nominal Z plane. This applies for flat planar pre-cuts; where non-flat planar cuts are provided, such regular shapes will not be provided.

It is preferred that the body comprises a third set of parallel planar partial pre-cuts in a third orientation. Again, it is preferred that the pre-cuts are regularly spaced, and the dimensions set out above in relation to the first and second sets of partial pre-cuts are equally applicable to the third set.

The third set may suitably be provided at a third orientation which is substantially perpendicular to both the first and second set of pre-cuts. Thus it could be said that the third set of pre-cuts lies on the Z plane, relative to the X and Y planes of the first and second sets respectively. Where three such sets are provided, the resultant selectively removable portions will be generally cuboids. Where the spacing between the planar partial pre-cuts are the same in each of the three sets, the resultant selectively removable portions will be substantially cubic.

It is of course possible to provide more than three sets of partial pre-cuts, and vary the angles between the pre-cuts to increase resolution and provide for a greater control over the shape and size of the selectively removable portions. However, where more than three sets are provided, the engineering difficulties in terms of physically forming the pre-cuts and also in retaining the general structural integrity of the body become considerable. In fact, even providing three sets of cuts in the X, Y and Z planes (i.e. a 3D pre-cut body) is somewhat difficult to achieve, and it is a significant aspect of the present invention that this has made possible.

As mentioned above, the spacing of the parallel planar partial pre-cuts, in particular the spacing between each pre-cut plane, dictates the size and shape of the selectively removable portions. A spacing of 20 mm, for example, in all 3 sets of a 3D pre-cut body provides for portions which are cubes of approximately 20 mm in each dimension. This allows a medical practitioner to remove cube shaped portions of foam to shape the body to the desired shape for wound packing, and to achieve a fit to the shape of the wound to within 20 mm. Alternatively, blocks of 20×20×10 mm may be a suitable shape allowing increased resolution one dimension, but retaining a relatively manageable number of portions. It is, of course, generally desirable to allow the medical practitioner to shape the body of wound packing material as closely as possible to the desired shape for wound packing, but this must be balanced against the need for ease of manufacture and simplicity of handling. It has been found that such a balance can be achieved using dimensions of from 10 to 20 mm for the removable portions.

It should be pointed out that in certain instances it may be sufficient to have the ability to remove portions to achieve a far less precise shape of body of wound packing material. In such situations a body comprising three sets of pre-cuts may not be required, and a body comprising one or two sets of parallel planar partial pre-cuts may provide sufficient scope for customisation of shape.

However, it is an objective of the present invention to provide a wound packing material which is highly customisable, and that a body comprising three or more sets of parallel planar partial pre-cuts is generally preferred.

Accordingly, in a particularly preferred embodiment the present invention provides a wound packing material comprising a body of a porous material, the body comprising frangible regions defining a plurality of selectively removable cuboidal portions, the frangible regions being defined by partial pre-cuts provided in the body of the body.

Preferably the body is entirely comprised of selectively removable cuboidal portions interconnected by frangible regions, each of the edges of the cuboids being 5 to 30 mm, preferably from 10 to 24 mm, especially from 10 to 20 mm.

More preferably the cuboidal portions are cubic and have an edge length of from 5 to 30 mm, preferably from 10 to 24 mm, especially from 10 to 20 mm.

Suitably the body is generally cuboidal in shape, prior to the removal of any selectively removable portions. The body may suitably be a cube, or it may be a rectangular cuboid or square cuboid. Various shapes of body may be useful for different wound shapes and sizes. Typically NPWT foam is provided as a rectangular cuboid of approximate dimensions 200×100×30 mm, and this is a suitable shape for the body of the present invention. For such a shape and size, portions of approximately 20×20×10 mm are very suitable to allow customisation of shape.

In a further aspect the present invention provides a method of manufacture of a wound packing material, the method comprising the steps of:
  providing a body of a porous wound packing material;
  forming at least one partial pre-cut in a first orientation in said body, said at least one partial pre-cut severing regions of the body to leave frangible regions of the body, the frangible regions allowing the portions to be selectively removed from the body.

Preferably the at least one partial pre-cut is a parallel planar partial pre-cut.

Preferably the at least one partial pre-cut is formed by die cutting.

The die cutting may involve providing at least one blade and pushing said blade through the body to cut a region of the body and leave at least one frangible region.

It is preferred that the die cutting involves providing a plurality of blades in a suitable arrangement to provide desired partial pre-cuts and frangible regions. Dimensions and other details of the partial pre-cuts are set out above.

Suitably the blades have a length great enough to pass completely through the body. It should be noted that the body may be compressed as it is cut, and therefore the blades need only be long enough to pass completely through the body as it is compressed in the cutting process. Alternatively the blades may be shorter where it is not desirable to cut all the way through the body, or where cuts from two sides will be made to cut completely through the body; in the latter case the blades will generally have a length of approximately half of the relevant dimension of the compressed body to be cut.

The blades may suitably be arranged as an array of a set of parallel planar flat blades, the set comprising a plurality of series of individual flat blades arranged in a plane, each individual flat blade having a width corresponding to the width of the region to be severed, and a gap between the individual flat blades corresponding to the width of the frangible region. Suitable details of the blades are set out above.

Suitably the method involves the step of forming a second partial pre-cut in a second orientation, especially a second set of partial pre-cuts as discussed above. Preferably the second orientation is perpendicular to the first orientation. Preferably the second partial pre-cut is a parallel planar partial pre-cut.

Suitably the method involves the step of forming a third partial pre-cut in a third orientation, especially a third set of partial pre-cuts as discussed above. Preferably the third orientation is perpendicular to the first and second orientations. Preferably the third partial pre-cut is a parallel partial planar pre-cut.

Thus the method may involve providing three partial pre-cuts in nominal X, Y and Z planes. Suitably the X, Y and Z planes are congruent with the faces of the body, where the body is a cuboid.

Suitably the method involves forming partial pre-cuts to define a plurality of regularly shaped and sized cuboidal portions interconnected by frangible regions. Suitably the entire body is formed of selectively removable cuboidal portions. Suitably the cuboidal portions are cubes.

In certain embodiments two or more sets of pre-cuts can be made simultaneously. This can be suitably carried out using a single array of blades comprising two sets of blades in two orientations, e.g. an array of cruciform blades.

Where there is a risk of excessive distortion to the body during the cutting process it is useful to support the foam structure during the cutting process.

In a further aspect of the present invention there is provided a method of preparing a wound packing material comprising the steps of:
  providing a wound packing material as set out above; and
  removing portions of the body of said would packing material such that the body is a desirable shape.

Preferably the body is shaped to approximately fit the shape of a wound to be packed.

Preferably the portions are removed manually, i.e. without the use of tools.

In a further aspect the present invention provides a method of treating a wound comprising the steps of;
  providing a wound packing material as set out above;
  removing portions of the body of said would packing material such that the body is a desirable shape to fit within said wound; and
  packing the wound with said wound packing material.

Preferably the method provides the step of applying a negative pressure to the wound through the wound packing material, i.e. the method is NPWT. In general this can be achieved by providing a substantially fluid impermeable sheet over the wound and wound dressing, thus defining a sealed volume, and applying a negative pressure inside said sealed volume. The seal need not be completely hermetic, but should be sufficient to allow a suitable negative pressure to be sustained. The source of negative pressure, e.g. a pipe form a vacuum pump, is provided at a position such that it draws fluids from the wound bed through the wound packing material.

Suitably the negative pressure is in the range of from 80 to 125 mm Hg below ambient atmospheric pressure.

In a further aspect the present invention provides the use of a wound packing material as set out above in wound treatment, especially NPWT.

BRIEF DESCRIPTION OF THE DRAWINGS

Embodiments of the present invention will now be described, by way of example only, with reference to the accompanying drawings, in which.

DETAILED DESCRIPTION OF SOME EXEMPLIFYING EMBODIMENTS

Figure 1:
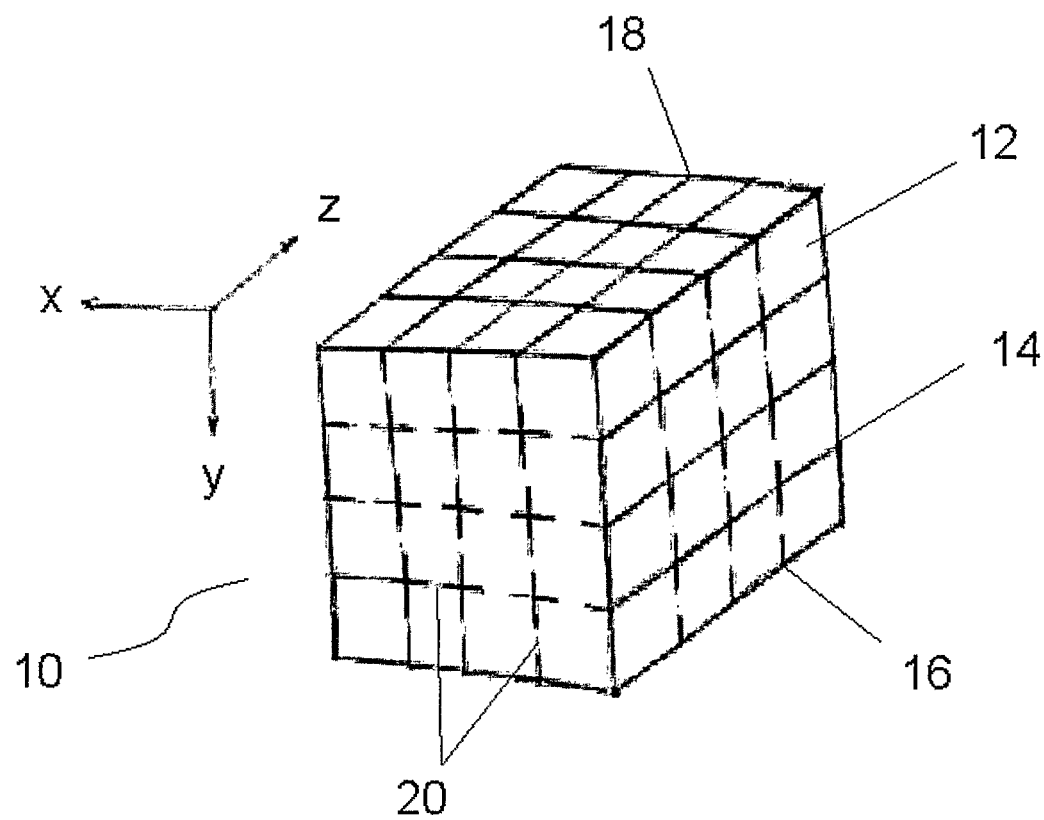
FIG. 1 shows a body of porous wound packing material after being pre-cut in the x, y and z dimensions.

As shown in FIG. 1, a body 10 of porous material, such as foam, is generally a cube in shape having three dimensions, x, y and z. The porous material is suitable for wound packing. The material may be reticulated polyurethane foam of very high free internal volume. The body 10 could be a different shape, e.g. a comparatively flat cuboid, which is a conventional shape for foams for NPWT.

Figure 2:
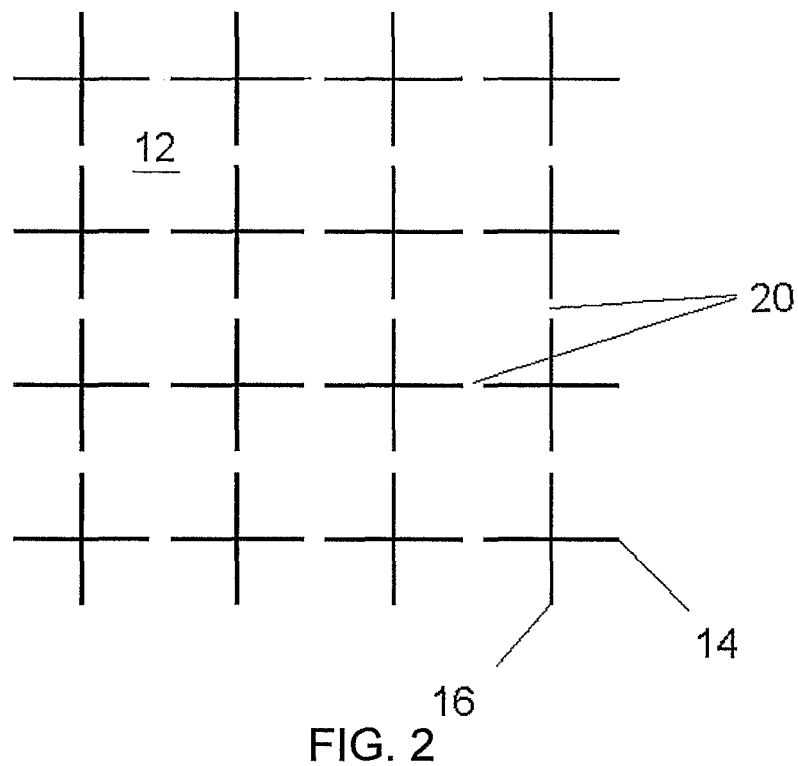
FIG. 2 schematically shows the set of pre-cuts in the x and y dimension.
Figure 3:
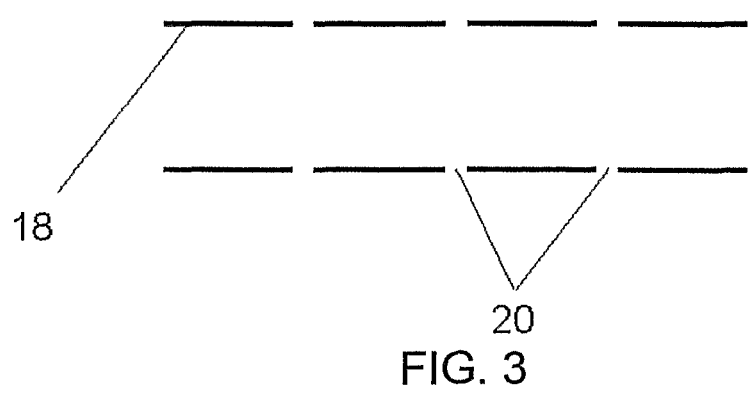
FIG. 3 schematically shows the sets of pre-cuts in the z dimension.

As shown in FIG. 2, the body 10 is partially pre-cut by a suitable cutting technique, such as die cutting (though other techniques may be useable), in the planes in the x and y dimensions to define a first and second set of parallel planar partial pre-cuts 14, 16. The body 10 is also partially pre-cut in the z dimension to define a third set of parallel planar partial pre-cut 18. The three sets of partial pre-cuts 14, 16, 18 define individual cubic portions 12 of approximately equal volume.

The three sets of partial pre-cuts 14, 16, 18 are intermittent, the gaps in the pre-cuts defining frangible regions 20 on each internal face of each portion 12 (in other words they are perforated for easy removal of the portions). The frangible regions 20 connect adjacent portions 12 together thereby to ensure the portions 12 remain connected together when the body 10 is stored, compressed or extended, i.e. when being used as a wound packing in NPWT.

The frangible regions 20 extend between face sides of each portion 12 and are elongate. The thickness of each frangible region 20 is suitable to provide adequate strength to ensure adjacent portions 12 remain connected when the body 10 is being compressed or extended during normal use, whilst allowing one or more portions 12 to be easily pulled from the body 10 by compromising the integrity of the frangible regions 20 attaching the portion 12 to the body. For typical NPWT foams, a frangible region of approximately 2 mm of thickness provides a good compromise of strength versus tearability.

One or more portions 12 can be selectively removed by hand from the body 10 to shape the body 10 for a particular wound packing application. Advantageously, cutting tools such as knives, scalpels and scissors are not required to shape the body 10 of porous material.

Figure 4:
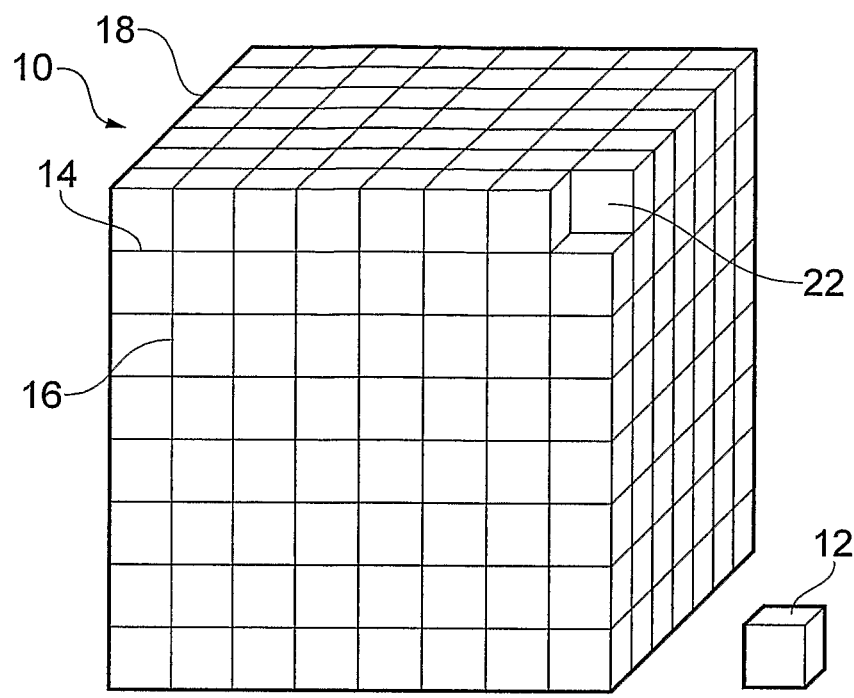
FIG. 4 shows a body with a single portion removed.
Figure 5:
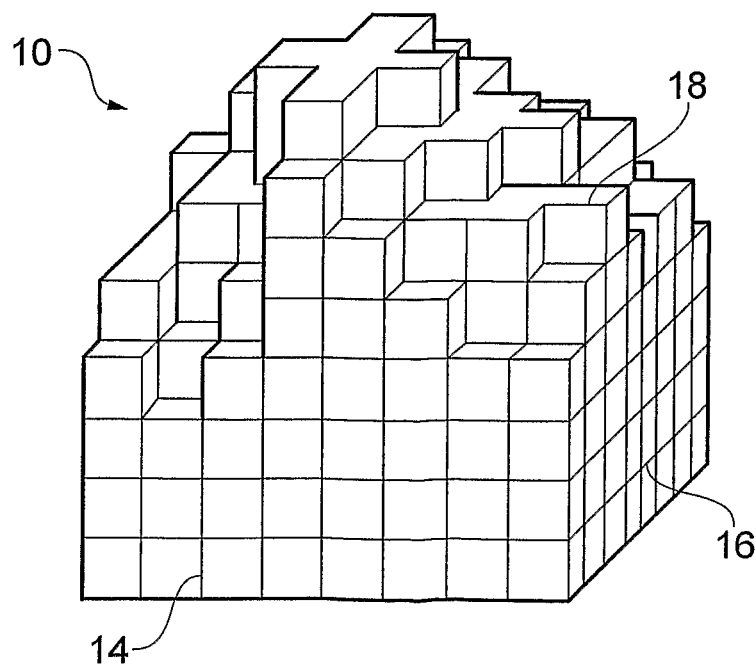
FIG. 5 shows the body of FIG. 4 with a plurality of portions removed.

As shown in FIGS. 4 and 5, the body 10 is a cube of volume 448000 mm$^3$, which is pre-cut in the x, y and z dimensions to define 448 (i.e. 7×8×8) equally sized 1000 mm$^3$ portions 12 (i.e. 10×10×10 mm). Adjacent portions 12 are connected by a frangible portion 20 of 2 mm thick porous material (not shown).

The frangible regions 20 ensure the body 10 retains its structural integrity for storage and handling purposes whilst allowing one or more portions 12 to be selectively removed therefrom. FIG. 4 shows a single portion 12 removed from the body 10 to leave a hole 22, whilst FIG. 5 shows a plurality of portions 12 removed from the body 10 to selectively shape the body 10 for a particular application of wound packing. The body 10 may be shaped to complement the external contours of a patient or to fit in a cavity.

Of course, the dimensions of the body 10 and the portions 12 may be different to those described above for a particular application and the number and orientation of partial pre-cuts lines 14, 16, 18 may be varied and may be planar or curved to define regular or irregular portions 12 accordingly.

To form a wound packing material similar to the above the following general process may be used. The present process describes a process for converting a single cuboid block of foam into 6 cuboidal wound packing material bodies. The block is initially approximately 200 mm by 100 mm by 180 mm and is cut into 6 blocks of 200 mm by 100 mm by 30 mm. It will be apparent that variations of this method could be used to manufacture wound packing materials of a great variety of different shapes and sizes, and having varying portion size and shapes.

A body of porous material is provided which has the dimensions set out above.

Figure 6:
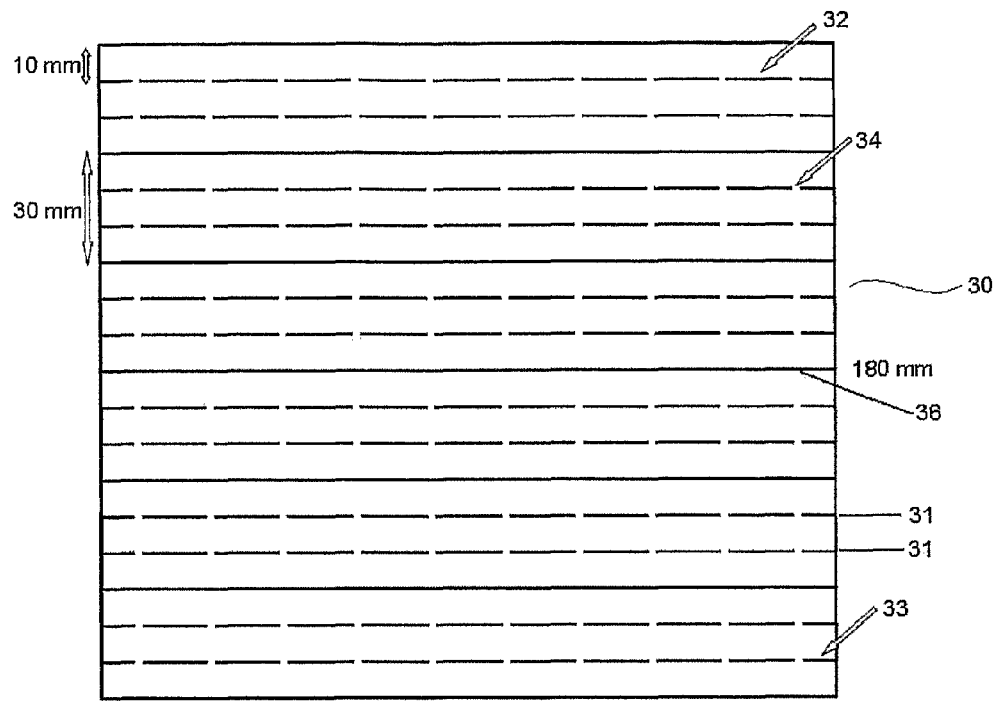
FIG. 6 shows a first array of a set of blades suitable for forming a partial pre-cut in a first orientation in a body of wound packing material.

A first set of parallel planar partial pre-cuts is made in the body using an array of blades 30. The pre-cuts are made perpendicular to, and into, a first face of the body The array (FIG. 6) comprises a number of planes 31 made up of a series of 18 mm wide flat blades 32, and a 9 mm blade 33 at each end of the plane; a gap 34 of 2 mm is provided between each blade in the series. A gap of 10 mm is left between each plane of blades. The array also comprises 5 continuous 100 mm long planar blades 36 which acts to cut the initial block completely into 6 smaller blocks.

The first set of partial pre-cuts is achieved by placing the block of foam against the array of blades 30 and urging the blades into and through the block. The pressure required may be generated by a hydraulic press (also known as a clicker press). This is a conventional form of die cutting and the necessary apparatus and techniques are well known to one skilled in the art.

Figure 7:
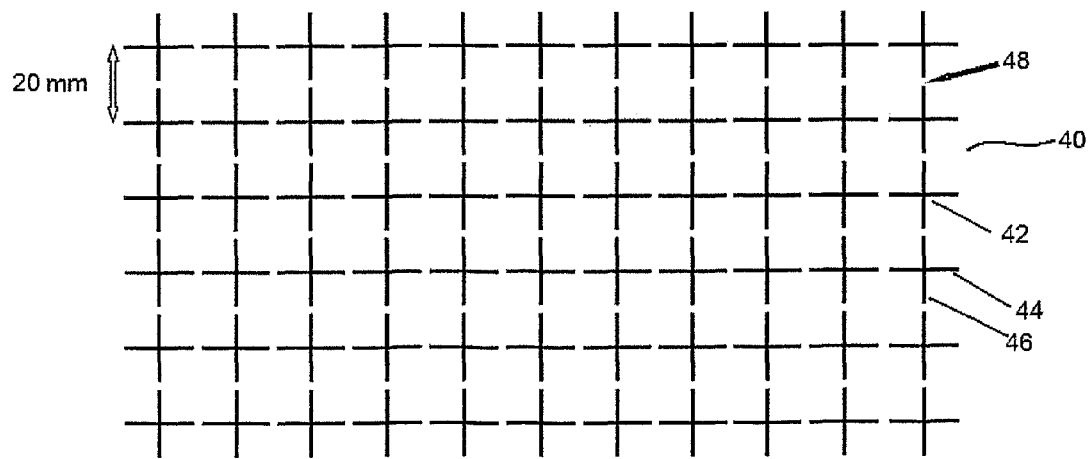
FIG. 7 shows a second array of sets of blades suitable for making second and third sets of partial pre-cuts in a body of wound packing material in second and third orientations.

Second and third sets of partial pre-cuts are made using a second array 40 of blades (see FIG. 7). In the second array a plurality of cruciform blades 42 are provided. Due to the shape and arrangement of the blades 42, the array is suitable to make two sets of parallel planar partial pre-cuts in two orientations, which are perpendicular to each other. Thus, in one cutting action, two sets of parallel planar partial pre-cuts are made. Each cruciform blade 42 comprises two 18 mm long linear blade elements 44,46 intercepting at each of their midpoints at a right angle to define the cruciform blade.

The cruciform blades are arranged in the array to form a square matrix with gaps 48 of 2 mm provided between each cruciform blade.

As with the first cut, the second cut is made by applying pressure to drive the blades 42 through the body.

The length of the blades in the first and second array are sufficient to pass completely through the body and emerge at the other side.

This process forms 6 cuboids of foam measuring 200 mm×100 mm×30 mm, which are each formed of cuboids measuring approximately 20 mm×20 mm×10 mm, each of the cuboid portions being interconnected with adjacent portions by frangible regions of approximately 2 mm thickness.

It should be noted that where a generally cubic body of foam is being prepared the order of the cuts is not particularly significant as the cube is equally structurally stable in all 3 dimensions. However, when preparing a body with a relatively thin minor dimension, as set out in the method above, it is important that the first cut made is the one perpendicular to the plane of the thin dimension (i.e. the smallest face of the cuboid), or that the shape of the block is supported as the cut is made. If the order is reversed, or the block shape is not supported, there is generally an unacceptable amount of crushing and/or corrugation of the body resulting in a significant distortion to the desired cut geometry.

The result of this process is a wound packing material which can be custom shaped by manually removing cuboid portions by tearing the frangible regions interconnecting the portions making up the body. This allows a medical practitioner to shape the body of wound packing material to fit the wound to be packed or dressed. Once the wound packing material has been shaped appropriately, the wound can be dressed for NPWT.

What is claimed is:

1. A wound packing material comprising:
    a body of porous material having a first configuration and a second configuration, the body in the first configuration comprising:
    an X dimension spanning the entirety of the body in an plane parallel to an X plane containing the X dimension;
    a Y dimension spanning the entirety of the body in an plane parallel to a Y plane containing the Y dimension; and
    a Z dimension spanning the entirety of the body in any plane parallel to a Z plane containing the Z dimension;
    wherein the X, Y, and Z dimensions are each oriented orthogonal to each other and the X, Y, and Z planes are each oriented orthogonal to each other;
    frangible regions defining a plurality of portions of porous material, the frangible regions allowing the portions to be selectively removed from the body,
    wherein each of the plurality of portions defined by the frangible regions is configured to be selectively removed to change shape of the body in the X, Y, and Z dimensions from the first configuration to the second configuration wherein:
        the body in the X dimension in at least one plane parallel to the X plane has at least some portion but not all portions of porous material removed;
        the body in the Y dimension in at least one plane parallel to the Y plane has at least some portion but not all portions of porous material removed; and
        the body in the Z dimension in at least one plane parallel to the Z plane has at least some portion but not all portions of porous material removed.

2. The wound packing material of claim 1 wherein the portions can be removed manually.

3. The wound packing material of claim 1 wherein the frangible regions are defined by partial pre-cuts formed in the body.

4. The wound packing material of claim 3 wherein the partial pre-cuts define a repeating pattern of severed regions with intervening frangible regions.

5. The wound packing material of claim 4 wherein the severed regions have a width of from 10 mm to 30 mm and the remaining frangible regions have a width of from 1 mm to 5 mm.

6. The wound packing material of claim 4 wherein each individual pre-cut severs from 15 to 19 mm and leaves a frangible region of from 1 to 5 mm between it and the adjacent pre-cut.

7. The wound packing material of claim 1 wherein the wound packing material is formed substantially from a wound packing foam suitable for use in negative pressure wound therapy (NPWT).

8. The wound packing material of claim 1 comprising a plurality of partial pre-cuts in a generally planar arrangement.

9. The wound packing material of claim 8 wherein the partial pre-cuts are flat planar partial pre-cuts.

10. The wound packing material of claim 8 wherein the body comprises a first set of substantially parallel planar partial pre-cuts in a first orientation.

11. The wound packing material of claim 10 wherein the planar pre-cuts of the set are regularly spaced.

12. The wound packing material of claim 11 wherein the spacing between the parallel planar pre-cuts in the set is 30 mm or less.

13. The wound packing material of claim 10 wherein the body comprises a second set of parallel planar partial pre-cuts in a second orientation.

14. The wound packing material of claim 13 wherein the second set of parallel planar partial pre-cuts is provided at a second orientation which is substantially perpendicular to the first orientation.

15. The wound packing material of claim 13 wherein the body comprises a third set of parallel planar partial pre-cuts in a third orientation.

16. The wound packing material of claim 15 wherein the third set of parallel planar partial pre-cuts is provided at a third orientation which is substantially perpendicular to both the first and second set of pre-cuts.

17. The wound packing material of claim 8 wherein the set of substantially planar pre-cuts comprises a plurality of planar pre-cuts spaced from one another by a spacing, each planar pre-cut comprising a series of individual pre-cuts, each individual pre-cut being spaced from the adjacent pre-cut by a gap.

18. The wound packing material of claim 1 wherein the body comprises partial pre-cuts formed by die-cutting.

19. The wound packing material of claim 1 wherein the body is entirely comprised of selectively removable cuboidal portions each having a cubic shape interconnected by frangible regions.

20. The wound packing material of claim 19 wherein the cuboidal portions are cubic and have an edge length of from 5 to 30 mm.

21. A method of treating a wound comprising;
    providing the wound packing material of claim 1;
    removing portions of the body of said wound packing material in the X dimension, the Y dimension, and the Z dimension such that the body is a desirable shape to fit within said wound; and packing the wound with said wound packing material.

22. The method of claim 21 comprising applying a negative pressure to the wound through the wound packing material.

23. The apparatus of claim 1, wherein the body comprises a set of partial pre-cuts in the x dimension.

24. The apparatus of claim 23, wherein the body further comprises a set of partial pre-cuts in the y dimension.

25. The apparatus of claim 24, wherein the body further comprises a set of partial pre-cuts in the z dimension.

26. A method of manufacture of a wound packing material, the method comprising:
    providing a body of porous wound packing material, the body comprising an X dimension, a Y dimension, and a Z dimension;
    forming at least one partial pre-cut in said body of porous wound packing material to construct a wound packing material as recited in claim 1.

27. The method of claim 26 wherein the at least one partial pre-cut is formed by die cutting.

28. The method of claim 27 wherein the die cutting involves providing a plurality of blades in a suitable arrangement to provide the desired partial pre-cuts and frangible regions.

29. The method of claim 28 wherein blades are arranged as an array of a set of parallel planar flat blades, the set comprising a plurality of series of individual flat blades arranged in a plane arranged parallel to one another, each individual flat blade having a width corresponding to the width of the region to be severed, and a spacing between adjacent blades corresponding to the width of the frangible region.

30. The method of claim 26 comprising forming a second partial pre-cut in a second orientation.

31. The method of claim 30 wherein the second orientation is perpendicular to the first orientation.

32. The method of claim 30 comprising forming a third partial pre-cut in a third orientation.

33. The method of claim 32 wherein the third orientation is perpendicular to the first and second orientations.

34. The method of claim 26 comprising providing three sets of parallel planar partial pre-cuts in the X dimension, the Y dimension and the Z dimension.

35. The method of claim 26 comprising forming partial pre-cuts to define a plurality of regularly shaped and sized cuboidal portions interconnected by frangible regions.

36. A method of preparing a wound packing material comprising:
    providing a wound packing material as recited in claim 1 and
    removing portions of the body of said wound packing material such that the body is a desirable shape.

37. The method of claim 36 wherein the portions are removed manually.

* * * * *